(12) United States Patent
Sim et al.

(10) Patent No.: US 10,494,346 B2
(45) Date of Patent: Dec. 3, 2019

(54) SUBSTITUTED PYRIMIDINE-4-CARBOXYLIC ACIDS HAVING ANTICANCER ACTIVITY

(71) Applicants: KOREA INSTITUTE OF SCIENCE AND TECHNOLOGY, Seoul (KR); INDUSTRY-UNIVERSITY COOPERATION FOUNDATION HANYANG UNIVERSITY, Seoul (KR)

(72) Inventors: Tae Bo Sim, Seoul (KR); Woo Young Hur, Seoul (KR); Ho Jong Yoon, Seoul (KR); Chi Man Song, Seoul (KR); In Jae Shun, Seoul (KR); Byeong Yun Lim, Seoul (KR); Han Na Cho, Seoul (KR); Seung Hye Choi, Seoul (KR); Gu Kong, Seoul (KR); Jeong Yeon Lee, Seoul (KR)

(73) Assignees: KOREA INSTITUTE OF SCIENCE AND TECHNOLOGY, Seoul (KR); INDUSTRY-UNIVERSITY COOPERATION FOUNDATION HANYANG UNIVERSITY, Seoul (KR)

(*) Notice: Subject to any disclaimer, the term of this patent is extended or adjusted under 35 U.S.C. 154(b) by 0 days.

(21) Appl. No.: 16/090,072

(22) PCT Filed: Mar. 30, 2017

(86) PCT No.: PCT/KR2017/003463
§ 371 (c)(1),
(2) Date: Sep. 28, 2018

(87) PCT Pub. No.: WO2017/171421
PCT Pub. Date: Oct. 5, 2017

(65) Prior Publication Data
US 2019/0135765 A1  May 9, 2019

(30) Foreign Application Priority Data
Mar. 30, 2016  (KR) .................. 10-2016-0038606

(51) Int. Cl.
*A61K 31/505* (2006.01)
*C07D 239/42* (2006.01)
*C07D 405/12* (2006.01)
*C07D 409/12* (2006.01)
*A61P 35/00* (2006.01)
*C07D 403/12* (2006.01)

(52) U.S. Cl.
CPC .......... *C07D 239/42* (2013.01); *A61P 35/00* (2018.01); *C07D 403/12* (2013.01); *C07D 405/12* (2013.01); *C07D 409/12* (2013.01)

(58) Field of Classification Search
CPC .................... A61K 31/505; C07D 239/42
USPC ........................... 514/256; 544/322
See application file for complete search history.

(56) References Cited

U.S. PATENT DOCUMENTS

| 2005/0192294 A1 | 9/2005 | Rudolph et al. |
| 2009/0005393 A1 | 1/2009 | Angibaud et al. |
| 2015/0080568 A1 | 3/2015 | Chen et al. |
| 2015/0299189 A1 | 10/2015 | Tanaka et al. |

FOREIGN PATENT DOCUMENTS

| WO | 2009/006389 A2 | 1/2009 |
| WO | 2014/100818 A1 | 6/2014 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Hejun Lu et al., Structure-based design and synthesis of bicyclic fused-pyridines as MEK inhibitors, Bioorganic & Medicinal Chemistry Letters 24, Apr. 3, 2014, pp. 2555-2559.

* cited by examiner

*Primary Examiner* — Douglas M Willis
(74) *Attorney, Agent, or Firm* — Goldilocks Zone IP Law

(57) ABSTRACT

The present invention relates to a novel pyrimidine-4-carboxylic acid derivative having an anticancer activity, and the compound thereof is useful as a drug for treating and preventing tumor diseases,
wherein
the compound is represented by the Formula 1:

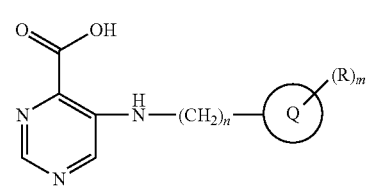

[Formula 1]

or a pharmaceutically acceptable salt thereof,
wherein:
Q is a C6-C15 aryl group; or a C4-C13 heteroaryl group, wherein the heteroaryl contains 1, 2 or 3 heteroatoms substituted with 1-3 heteroatom(s) selected from the group consisting of nitrogen, oxygen or sulfur;
R is a halogen; a C1-C10 haloalkyl substituted with 1-13 halogen atom(s); a C1-C10 alkoxy; a 5- or 6-membered heterocycloalkyl or (CH2)r-R1 wherein the heterocycloalkyl contains 1-2 heteroatom(s) selected from the group consisting of nitrogen and oxygen;
R1 is a hydrogen; a C1-C10 alkoxy; amino; mono(C1-C10 alkyl)amino; di(C1-C10 alkyl)amino; or —NHC(O)-phenyl;
n is 1, 2, 3, 4, 5, or 6; and
r is 0, 1, 2, 3, 4, 5, or 6; and
m is 0, 1, 2 or 3.

10 Claims, No Drawings

SUBSTITUTED PYRIMIDINE-4-CARBOXYLIC ACIDS HAVING ANTICANCER ACTIVITY

CROSS-REFERENCE TO RELATED APPLICATIONS

This application claims the benefit under 35 U.S.C. Section 371, of PCT International Application No. PCT/KR2017/003463, filed Mar. 30, 2017, which claimed priority to Korean Patent Application No. KR 10-2016-0038606, filed Mar. 30, 2016, the disclosures of which are hereby incorporated by the references.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISK

Not Applicable

BACKGROUND OF THE INVENTION

(1) Field of the Invention

The present invention relates to a novel pyrimidine-4-carboxylic acid derivative having histone demethylase inhibitor activity.

(2) Description of Related Art

Gene expression regulation occurs not only by direct chemical methylation change of DNA, but also by methylation of histone proteins linked to nucleosomes which are structures in which DNAs are highly condensed. Among enzymes relating to such epigenetic inheritance, histone demethylases attract much attention as promising anti-cancer drug targets.

Enzymes for selectively demethylating methyl groups linked to histone lysine may be broadly classified into the LSD class and the JmjC class. The LSD class is an amineoxidase using FAD as a co-factor, which is involved in demethylation of mono- and di-methyl lysine of H3K4. The JmjC class is an dioxygenase that has a Jumonji C (JmjC) domain and uses Fe (II) and alpha-ketoglutaric acid as co-factors, which is involved in demethylation of mono-, di- or tri-methyl lysine. Somatic mutation of histone demethylase was almost not found, but it was reported to be overexpressed in some carcinomas, which induces development of cancer. For example, RBP2 is an enzyme that demethylates di- and/or tri-methylation groups of histone H3 lysine 4 (H3K4me2/3), which facilitates expression of various genes (for example, TNC) relating to metastasis and serves as an essential epigenetic switch determining cancer metastasis. In addition, RBP2 is overexpressed in lung cancer tissue, genetic knockdown of RBP2 inhibits growth, movement, permeation and metastasis of lung cancer cells. Since research results demonstrating that, in lung cancer cell lines, RBP2 facilitates expression of cyclin D1 and E1, and expression of integrin-β1 associated with metastasis, were reported, inhibitory mechanisms of histone demethylase including RBP2 have attracted a great deal of attention as promising targets for novel anti-cancer drugs.

Meanwhile, WO 2014/100818 discloses that a novel pyrimidine-4-carboxylic acid derivative represented by the following Formula A has inhibitory activity against histone demethylase, and is useful for the treatment of tumor diseases such as prostate cancer, breast cancer, bladder cancer, lung cancer, and/or melanoma and the like.

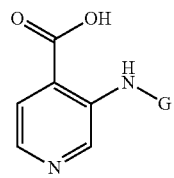

[Formula A]

However, it has not been reported to date that the compound having a pyrimidine-4-carboxylic acid core structure suggested by the present invention has histone demethylase inhibitor activity.

Thus, it is one object of the present invention to provide a novel compound having a core structure of pyrimidine-4-carboxylic acid.

Also, it is another object of the present invention to provide a pharmaceutical use of the novel compound as a drug for treating or preventing tumor diseases, based on inhibitory activity of the compound against histone demethylase.

BRIEF SUMMARY OF THE INVENTION

In order to accomplish the objects described above, in one aspect, the present invention provides a pyrimidine-4-carboxylic acid compound represented by the following Formula 1, a hydrate thereof, solvate thereof, isomer thereof, racemate thereof or pharmaceutically acceptable salt thereof:

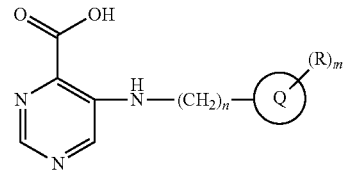

[Formula 1]

wherein

Q is a $C_6$-$C_{15}$ aryl group; or a $C_4$-$C_{13}$ heteroaryl group substituted with 1-3 heteroatom(s) selected from the group consisting of N, O and S;

R is a halogen atom; a $C_1$-$C_{10}$ haloalkyl group substituted with 1-13 halogen atom(s); a $C_1$-$C_{10}$ alkoxy group; a 5- or 6-membered heterocycloalkyl group substituted with 1-2 heteroatom(s) selected from the group consisting of N and O; or —$(CH_2)_r$—$R^1$;

$R^1$ is a hydrogen atom; a $C_1$-$C_{10}$ alkoxy group; an amino group; a mono($C_1$-$C_{10}$ alkyl)amino group; a di($C_1$-$C_{10}$ alkyl) amino group; or —NHC(O)—$C_6H5$;

n and r are an integer of 0 to 6; and m is an integer of 0 to 3.

In another aspect, the present invention provides a theoretical or prophylactic agent for a tumor disease containing, as an active ingredient, a compound selected from the group consisting of the pyrimidine-4-carboxylic acid compound represented by Formula 1, a hydrate thereof, solvate thereof, isomer thereof, racemate thereof and pharmaceutically acceptable salt thereof.

Advantageous Effects

The pyrimidine-4-carboxylic acid compound according to the present invention is highly capable of inhibiting histone demethylase such as KDM5A. Accordingly, the pyrimidine-4-carboxylic acid compound of the present invention can be used as an active ingredient of a pharmaceutical composition for treating or preventing a tumor disease such as prostate cancer, breast cancer, bladder cancer, lung cancer, and melanoma.

DETAILED DESCRIPTION OF THE INVENTION

The present invention relates to a pyrimidine-4-carboxylic acid compound represented by the following Formula 1:

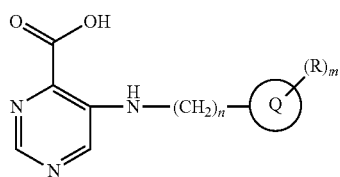

[Formula 1]

wherein

Q is a $C_6$-$C_{15}$ aryl group; or a $C_4$-$C_{13}$ heteroaryl group substituted with 1-3 heteroatom(s) selected from the group consisting of N, O and S;

R is a halogen atom; a $C_1$-$C_{10}$ haloalkyl group substituted with 1-13 halogen atom(s); a $C_1$-$C_{10}$ alkoxy group; a 5- or 6-membered heterocycloalkyl group substituted with 1-2 heteroatom(s) selected from the group consisting of N and O; or —$(CH_2)_r$—$R^1$;

$R^1$ is a hydrogen atom; a $C_1$-$C_{10}$ alkoxy group; an amino group; a mono($C_1$-$C_{10}$alkyl)amino group; a di($C_1$-$C_{10}$ alkyl) amino group; or —NHC(O)—$C_6H5$;

n and r are an integer of 0 to 6; and m is an integer of 0 to 3.

The compound represented by the following Formula 1 according to the present invention may have one or more chiral centers and, in the case of such a compound, an enantiomer or diastereomer may be present. Accordingly, the present invention includes respective isomer compounds, and a mixture or racemate of these isomers.

In addition, the present invention includes a radioactive derivative in which a radioactive element is introduced into the compound represented by Formula 1 and the radioactive compound is useful for the biotherapy field through imaging.

In addition, a pharmaceutically acceptable salt can be produced from the compound represented by Formula 1 according to the present invention by an ordinary method well-known in the art. For example, non-toxic inorganic acids such as hydrochloric acid, bromic acid, sulfonic acid, amidosulfuric acid, phosphoric acid and nitric acid, or non-toxic organic acids such as propionic acid, succinic acid, glycolic acid, stearic acid, lactic acid, tartaric acid, citric acid, para-toluenesulfonic acid and methane-sulfonic acid, and pharmaceutically acceptable salts of these salts can be formed.

In addition, a part of the compound represented by Formula 1 according to the present invention can be crystallized or re-crystallized from a solvent such as aqueous and organic solvents. In this case, a solvate can be formed. Not only compounds containing a variety of amounts of water that can be produced by a method such as lyophilization, but also hydrates and stoichiometric solvates fall into the scope of the present invention.

Substituents used to define the compound represented by Formula 1 according to the present invention will be described in more detail.

As used herein, the terms "halo" and "halogen atom", which mean chlorine, fluorine, bromine or iodine, can be used interchangeably.

As used herein, the term "alkyl" means a linear, branched or cyclic aliphatic saturated hydrocarbon group having 1 to 10 carbon atom(s), preferably 1 to 6 carbon atom(s), more preferably 1 to 4 carbon atom(s). Specifically, examples of the alkyl group include a methyl group, an ethyl group, a normal-propyl group, an iso-propyl group, a cyclopropyl group, a cyclopropylmethyl group, a normal-butyl group, an iso-butyl group, a tert-butyl group, a cyclobutyl group, a normal-pentyl group, an iso-pentyl group, a neopentyl group, a tert-pentyl group, a cyclopentyl group, a normal-hexyl group, an iso-hexyl group, a cyclohexyl group, a normal-heptyl group, a normal-octyl group and the like.

As used herein, the term "alkoxy" means an alkyl group of carbon linked to oxygen wherein the alkyl is defined as above.

As used herein, the term "haloalkyl" includes all linear and branched carbon chains that include 1 to 13 halogen atom(s) such as fluorine, chlorine, bromine and iodine, and have 1 to 10 carbon atom(s). Preferred haloalkyl groups include a fluoromethyl group, a trifluoromethyl group, a 1,2-dichloroethyl group, a 1,1-dichloroethyl group, a pentafluoroethyl group and the like.

As used herein, the term "heterocycloalkyl" means a five- or six-membered, saturated or partially saturated aliphatic cyclic group that includes 1 to 2 heteroatom(s) selected from the group consisting of O and N. Specifically, examples of the heterocycloalkyl group include a tetrahydrofuranyl group, a 2,3-dihydrofuranyl group, a 2,5-dihydrofuranyl group, a pyrrolidinyl group, a 2,3-dihydropyrrolidinyl group, a 2,5-dihydropyrrolidinyl group, a tetrahydro-2H-pyranyl group, a 3,4-dihydro-2H-pyranyl group, a 4H-pyranyl group, a piperidinyl group, a 1,2,3,4-tetrahydropyridinyl group, a 1,4-dihydropyridinyl group, a piperazinyl group, an N-protected piperazinyl group, a morpholino group and the like. The N-protective group of piperazinyl may typically include a $C_1$-$C_{10}$ alkyl group.

As used herein, the term "aryl" means a mono-, di- or tri-cyclic aromatic hydrocarbon group having 6 to 15 carbon atoms. Specifically, examples of the aryl group include a phenyl group, a biphenyl group, a naphthalenyl group, an anthracenyl group, a phenanthrenyl group and the like.

As used herein, the term "heteroaryl" means a mono-, di- or tri-cyclic aromatic group that includes 1 to 3 heteroatom(s) selected from the group consisting of N, O and S, and has 4 to 13 carbon atoms. Examples of the heteroaryl include a pyrrolyl group, a pyrazolyl group, an imidazolyl group, a furanyl group, an oxazolyl group, an isoxazolyl group, a thiophenyl group, a thiazolyl group, an isothiazolyl group, a pyridinyl group, a pyrazinyl group, a pyridazinyl group, a pyrimidinyl group, an indolyl group, an isoindolyl group, an indazolyl group, a benzimidazolyl group, a benzothiazolyl group, a benzisothiazolyl group, a quinolinyl group, an isoquinolinyl group, a phthalazinyl group, a quinazolinyl group and the like.

The compound represented by Formula 1 is preferably a compound, wherein Q is an aryl group selected from the group consisting of phenyl, biphenyl and naphthalenyl; or a heteroaryl group selected from the group consisting of furanyl, thiophenyl, pyrazolyl, oxazolyl, isoxazolyl, pyridinyl, pyrimidinyl, pyridazinyl and indazolyl, R is a halogen atom selected from the group consisting of chlorine, fluorine, bromine and iodine; a trifluoromethyl group; an alkoxy group selected from the group consisting of methoxy, ethoxy, normal-propoxy, iso-propoxy and tert-butoxy; a heterocycloalkyl group selected from the group consisting of morpholino, piperidinyl, piperazinyl and N—($C_1$-$C_{10}$ alkyl)piperazinyl; or —($CH_2$)r-R, wherein $R^1$ is a hydrogen atom, a methoxy group, an ethoxy group, a propoxy group, an amino group, a methylamino group, a dimethylamino group, a diethylamino group or a benzamido group, n and r are an integer of 0 to 6, and m is an integer of 0 to 3.

The compound represented by Formula 1 is more preferably a compound, wherein Q is a phenyl group, a biphenyl group, a naphthalenyl group, a furanyl group, a thiophenyl group, a pyrazolyl group, a pyridazinyl group or an indazolyl group, R is chlorine, fluorine, a trifluoromethyl group, a methoxy group, a 4-ethylpiperazin-1-yl group, a methyl group, an ethyl group, a propyl group, a 2-(dimethylamino)ethyl group, a 3-(dimethylamino)propyl group or a 3-(benzamido) propyl group, N is 0 or 1, and M is 0, 1 or 2.

Specifically, examples of the pyrimidine-4-carboxylic acid compound represented by Formula 1 according to the present invention are given below:

5-(([1,1'-biphenyl]-4-ylmethyl)amino)pyrimidine-4-carboxylic acid;

5-((2,4-dimethoxybenzyl)amino)pyrimidine-4-carboxylic acid;

5-((3,4-dichlorobenzyl)amino)pyrimidine-4-carboxylic acid;

5-((furan-2-ylmethyl)amino)pyrimidine-4-carboxylic acid;

5-(((3-methylthiophen-2-yl)methyl)amino)pyrimidine-4-carboxylic acid;

5-((4-fluorobenzyl)amino)pyrimidine-4-carboxylic acid;

5-((3,5-bis(trifluoromethyl)benzyl)amino)pyrimidine-4-carboxylic acid;

5-((4-methoxybenzyl)amino)pyrimidine-4-carboxylic acid;

5-((4-methylbenzyl)amino)pyrimidine-4-carboxylic acid;

5-((3-fluorobenzyl)amino)pyrimidine-4-carboxylic acid;

5-((2-fluorobenzyl)amino)pyrimidine-4-carboxylic acid;

5-((1-propyl-1H-indazol-3-yl)amino)pyrimidine-4-carboxylic acid;

5-((1-(2-(dimethylamino)ethyl)-1H-indazol-3-yl)amino)pyrimidine-4-carboxylic acid;

5-((1-(3-benzamidopropyl)-1H-pyrazol-4-yl)amino)pyrimidine-4-carboxylic acid;

5-((l-methyl-1H-pyrazol-3-yl)amino)pyrimidine-4-carboxylic acid;

5-((l-methyl-1H-pyrazol-4-yl)amino)pyrimidine-4-carboxylic acid;

5-(pyridazin-3-ylamino)pyrimidine-4-carboxylic acid;

5-(naphthalen-1-ylamino)pyrimidine-4-carboxylic acid;

5-((1-(3-(dimethylamino)propyl)-1H-pyrazol-4-yl)amino)pyrimidine-4-carboxylic acid; and 5-((4-(4-ethylpiperazin-1-yl)phenyl)amino)pyrimidine-4-carboxylic acid.

Meanwhile, the present invention includes a pharmaceutical composition containing, as an active ingredient, the compound represented by the following Formula 1, a hydrate thereof, solvate thereof, isomer thereof, racemate thereof or pharmaceutically acceptable salt thereof.

The compound represented by Formula 1 exhibits excellent inhibitory activity against histone demethylase and can thus be used as a drug for preventing or treating tumor diseases induced by abnormal cell growth.

The protein histone demethylase may, for example, include KDM4A, KDM5A, KDM5B, KDM6B, LSD1 and the like.

Examples of the tumor diseases induced by abnormal cell growth according to the present invention include a variety of cancer diseases such as prostate cancer, breast cancer, bladder cancer, lung cancer, melanoma and the like.

The pharmaceutical composition of the present invention can be prepared into a formulation ordinarily used in the pharmaceutical field, for example, a formulation for oral administration such as a tablet, a capsule, a troche, a liquid/solution, a suspension or the like, or a formulation for parenteral administration, by incorporating, as an active ingredient, the compound represented by Formula 1, a hydrate thereof, solvate thereof, isomer thereof, racemate thereof or pharmaceutically acceptable salt thereof, and further adding an ordinary non-toxic pharmaceutically acceptable carrier, adjuvant, excipient or the like thereto.

The excipient that can be used for the pharmaceutical composition of the present invention includes a sweetener, a binder, a solubilizer, a solubilizing aid, a wetting agent, an emulsifier, an isotonic agent, an adsorbent, a disintegrant, an antioxidant, a preservative, a lubricant, a filler, a fragrance or the like. Examples of the excipient include lactose, dextrose, sucrose, mannitol, sorbitol, cellulose, glycine, silica, talc, stearic acid, stearin, magnesium stearate, magnesium aluminum silicate, starch, gelatin, tragacanth gum, alginic acid, sodium alginate, methyl cellulose, sodium carboxymethyl cellulose, agar, water, ethanol, polyethylene glycol, polyvinyl pyrrolidone, sodium chloride, calcium chloride, orange essence, strawberry essence, vanilla fragrance and the like.

In addition, the dosage of the compound according to the present invention applied to human may be determined depending on age, body weight, administration routes, health conditions and disease severity of patients. The dosage is generally 0.01 to 1,000 mg/day on the basis of an adult patient with a body weight of 70 kg and the compound may be administered at one time or multiple times (portion-wise) daily at a predetermined interval according to prescriptions of physicians or pharmacists.

Meanwhile, the present invention provides a method for preparing the compound represented by Formula 1.

The compound represented by Formula 1 according to the present invention can be prepared by a preparation method including a series of steps in accordance with the following Reaction Scheme 1:

[Reaction Scheme 1]

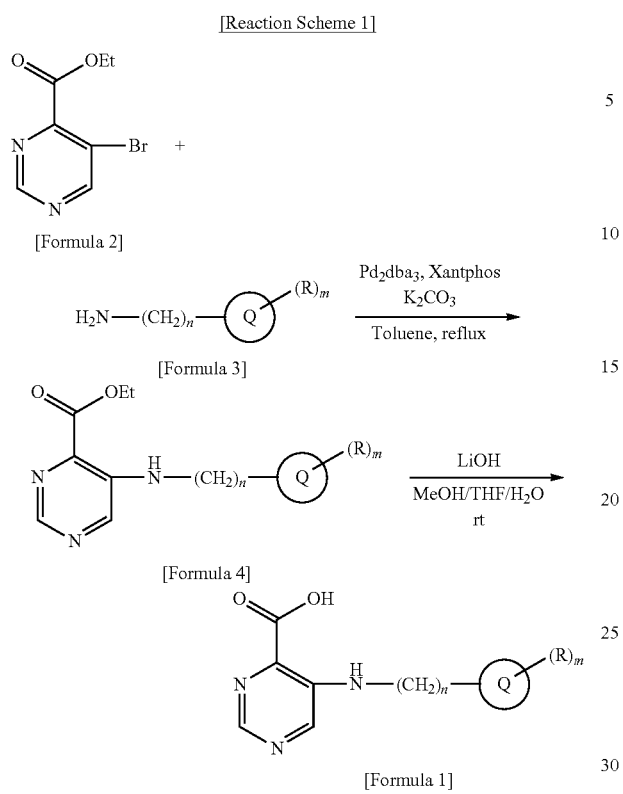

wherein Q, R, n and m are each defined as in Formula 1.

In accordance with Reaction Scheme 1 above, the compound represented by Formula 1 can be prepared by the preparation method according to the present invention including two steps using, as a starting material, bromine-substituted ethyl pyrimidine-4-carboxylate represented by Formula 2 above.

The first step includes reacting the bromine-substituted ethyl pyrimidine-4-carboxylate represented by Formula 2 with an appropriate amine compound represented by Formula 3 above in the presence of a base, a palladium catalyst and xantphos, to prepare an amine-substituted ethyl pyrimidine-4-carboxylate represented by Formula 4 above.

In this case, the base may be an inorganic base selected from the group consisting of hydroxides, oxides, carbonates, sulfates and the like of alkali metals or alkaline earth metals, and is preferably a carbonate of an alkali metal or alkaline earth metal such as calcium carbonate. A representative example of a useful palladium catalyst is tris(dibenzylideneacetone)dipalladium (0) ($Pd_2dba_3$). The reaction is preferably performed at a temperature of 70° C. to 150° C., more preferably at a reflux temperature of the solvent. The reaction solvent may be an ordinary organic solvent. Toluene, which is a representative example of an aromatic hydrocarbon, is used in the example of the present invention, but the solvent of present invention is not limited thereto.

The second step includes hydrolyzing the amine-substituted ethyl pyrimidine-4-carboxylate represented by Formula 4, to prepare the pyrimidine-4-carboxylic acid compound represented by Formula 1.

The hydrolysis may be carried out under acidic or basic conditions, preferably under basic conditions. A useful hydrolase may include an alkali metal hydroxide such as lithium hydroxide or sodium hydroxide. A hydrolysis temperature is about room temperature and is specifically maintained at a temperature of 20° C. to 30° C. A hydrolysis solvent may be a combined solvent of water and an organic polar solvent. In this case, the organic polar solvent may include one or more selected from the group consisting of $C_1$ to $C_4$ alcohol, tetrahydrofuran (THF), dimethylformamide (DMF), dimethylsulfoxide (DMSO) and the like.

The aforementioned present invention will be described in more detail with reference to the following Example. The following Example and Test Example are provided only for illustration of the present invention and should not be construed as limiting the scope of the present invention.

Example

Example 1: Synthesis of 5-(([1,1'-biphenyl]-4-ylmethyl)amino)pyrimidine-4-carboxylic Acid

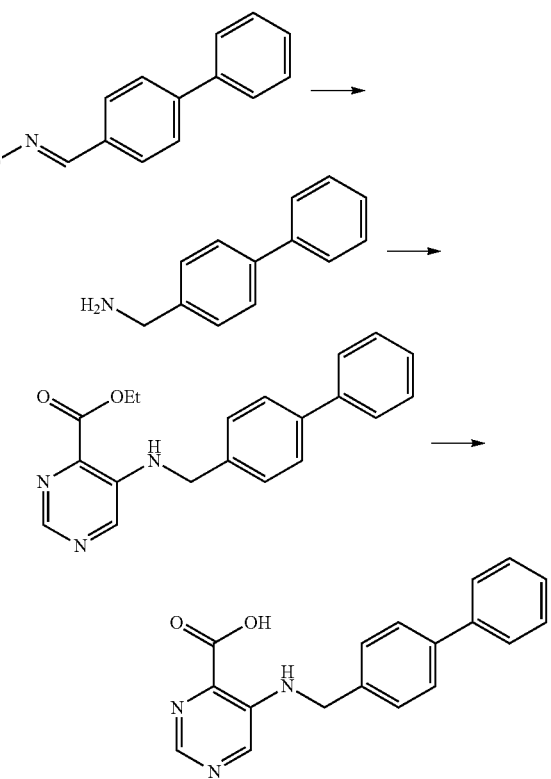

Step 1: [1,1'-biphenyl]-4-carbaldehyde Oxime $NH_2OH \cdot HCl$ (757 mg, 11.0 mmol) and $Na_2CO_3$ (873 mg, 8.23 mmol) were dissolved in water (4 mL), and the resulting solution was slowly added dropwise to a solution of [1,1'-biphenyl]-4-carbaldehyde (1,000 mg, 5.48 mmol) in ethanol (10 mL), followed by stirring at 105° C. for 30 minutes. After completion of the reaction, the reaction solution was allowed to cool to room temperature and was distilled under reduced pressure to remove ⅓ of the solvent, and the residue was diluted with water and extracted using ethyl acetate. The collected organic layer was dried over anhydrous magnesium sulfate and filtered, and the solution was concentrated under reduced pressure to obtain the titled compound as a white solid (1047.3 mg, 97% yield).

<sup>1</sup>H NMR (400 MHz, CHCl₃) δ 8.03 (s, 1H), 7.76-7.75 (m, 1H), 7.65-7.62 (m, 3H), 7.57-7.56 (m, 1H), 7.45-7.42 (m, 3H), 7.35-7.31 (m, 1H).

Step 2: [1,1'-biphenyl]-4-ylmethanamine

[1,1'-biphenyl]-4-carbaldehyde oxime (1,000 mg, 5.48 mmol) was dissolved in methanol (20 mL), and NaBH₄ (976.0 mg, 25.8 mmol) and NiCl₂.6H₂O (1022.1 mg, 4.3 mmol) were slowly added dropwise to the resulting solution, followed by stirring at room temperature for 30 minutes. After completion of the reaction, the reaction solution was diluted with a 1% NH₄OH solution and extracted using ethyl acetate. The collected organic layer was dried over anhydrous magnesium sulfate and filtered, and the solution was concentrated under reduced pressure. The obtained residue was purified by column chromatography (DCM:MeOH:NH₄OH=80:19:1) to obtain the titled compound as a yellow oil (2.59 g, 82% yield).

$^1$H NMR (400 MHz, CHCl₃) δ 7.61-7.53 (m, 4H), 7.44-7.30 (m, 5H), 3.87 (2H, s), 1.53 (br s, 2H).

Step 3: Ethyl 5-(([1,1'-biphenyl]-4-ylmethyl)amino)pyrimidine-4-carboxylate

Ethyl 5-bromopyrimidine-4-carboxylate (35.0 mg, 0.15 mmol), [1,1'-biphenyl]-4-ylmethanamine (30.0 mg, 0.18 mmol), K₂CO₃ (62 mg, 0.45 mmol) and toluene (1 mL) were charged in a sealed tube and the tube was then degassed. Xantphos (27 mg, 0.045 mmol) and Pd₂(dba)₃ (14 mg, 0.015 mmol) were added to the reaction solution, followed by stirring at 110° C. for 3 hours. After completion of the reaction, the reaction solution was allowed to cool to room temperature and filtered through a Celite pad using ethyl acetate. The filtrate was concentrated under reduced pressure and the obtained residue was purified by column chromatography (silica, MPLC:EtOAc:n-Hexane=20:80 to 50:50) to obtain the titled compound as a pale yellow solid (39.5 mg, 79% yield).

LC-MS m/z [M+H]⁺=334

Step 4: 5-(([1,1'-biphenyl]-4-ylmethyl)amino)pyrimidine-4-carboxylic Acid

Ethyl 5-(([1,1'-biphenyl]-4-ylmethyl)amino)pyrimidine-4-carboxylate (39.5 mg, 0.12 mmol) and LiCl (7.6 mg, 0.18 mmol) were added to a mix solution of methanol (1 mL), THF (1 mL) and H₂O (1 mL), followed by stirring at room temperature for 30 minutes. After completion of the reaction, the reaction solution was acidified with an aqueous 1N HCl solution. The acidized solution was extracted using a mix solution of chloroform/isopropanol (4:1). The collected organic layer was dried over anhydrous magnesium sulfate and filtered, and the solution was concentrated under reduced pressure to obtain the titled compound as a pale yellow solid (34.8 mg, 97%).

$^1$H NMR (400 MHz, DMSO-d₆) δ 8.48 (s, 1H), 8.01 (br s, 1H), 7.65-7.63 (m, 4H), 7.46-7.42 (m, 4H), 7.34 (t, J=8.0 Hz, 1H), 4.64 (s, 2H)

Example 2. Synthesis of 5-((2,4-dimethoxybenzyl)amino)pyrimidine-4-carboxylic Acid

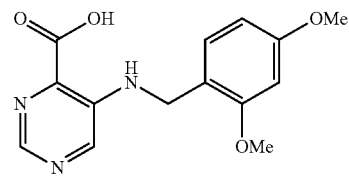 [SMILES: COc1ccc(CNc2cncnc2C(=O)O)c(OC)c1]

The titled compound was synthesized with reference to the method illustrated in Example 1, except that an appropriate amine was used instead of [1,1'-biphenyl]-4-ylmethanamine in step 2 of Example 1.
LC-MS m/z [M+H]⁺=290.

Example 3. Synthesis of 5-((3,4-dichlorobenzyl)amino)pyrimidine-4-carboxylic Acid

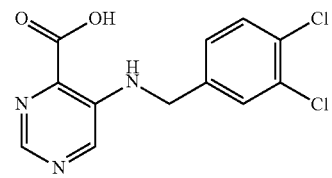 [SMILES: O=C(O)c1ncncc1NCc1ccc(Cl)c(Cl)c1]

The titled compound was synthesized with reference to the method illustrated in Example 1, except that an appropriate amine was used instead of [1,1'-biphenyl]-4-ylmethanamine in step 3 of Example 1.
LC-MS m/z [M+H]⁺=298

Example 4. Synthesis of 5-((furan-2-ylmethyl)amino)pyrimidine-4-carboxylic Acid

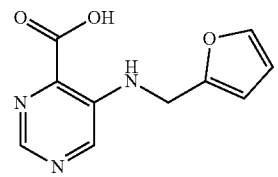 [SMILES: O=C(O)c1ncncc1NCc1ccco1]

The titled compound was synthesized with reference to the method illustrated in Example 1, except that an appropriate amine was used instead of [1,1'-biphenyl]-4-ylmethanamine in step 3 of Example 1.
LC-MS m/z [M+H]⁺=220

Example 5. Synthesis of 5-(((3-methylthiophen-2-yl)methyl)amino)pyrimidine-4-carboxylic Acid

The titled compound was synthesized with reference to the method illustrated in Example 1, except that an appropriate amine was used instead of [1,1'-biphenyl]-4-ylmethanamine in step 3 of Example 1.

LC-MS m/z [M+H]⁺=250

Example 6. Synthesis of 5-((4-fluorobenzyl)amino)pyrimidine-4-carboxylic Acid

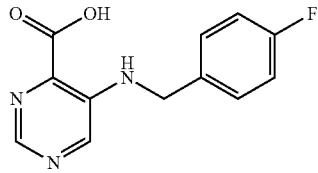 [SMILES: O=C(O)c1ncncc1NCc1ccc(F)cc1]

The titled compound was synthesized with reference to the method illustrated in Example 1, except that an appropriate amine was used instead of [1,1'-biphenyl]-4-ylmethanamine in step 3 of Example 1.

LC-MS m/z [M+H]⁺=248

Example 7. Synthesis of 5-((3,5-bis(trifluoromethyl)benzyl)amino)pyrimidine-4-carboxylic Acid

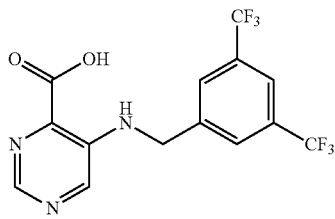 [SMILES: O=C(O)c1ncncc1NCc1cc(C(F)(F)F)cc(C(F)(F)F)c1]

The titled compound was synthesized with reference to the method illustrated in Example 1, except that an appropriate amine was used instead of [1,1'-biphenyl]-4-ylmethanamine in step 3 of Example 1.

LC-MS m/z [M+H]⁺=366

Example 8. Synthesis of 5-((4-methoxybenzyl)amino)pyrimidine-4-carboxylic Acid

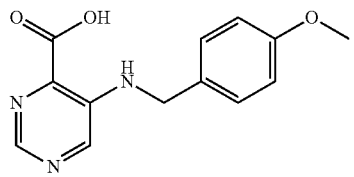 [SMILES: COc1ccc(CNc2cncnc2C(=O)O)cc1]

The titled compound was synthesized with reference to the method illustrated in Example 1, except that an appropriate amine was used instead of [1,1'-biphenyl]-4-ylmethanamine in step 3 of Example 1.

LC-MS m/z [M+H]⁺=260

Example 9. Synthesis of 5-((4-methylbenzyl)amino)pyrimidine-4-carboxylic Acid

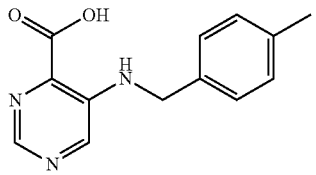 [SMILES: Cc1ccc(CNc2cncnc2C(=O)O)cc1]

The titled compound was synthesized with reference to the method illustrated in Example 1, except that an appropriate amine was used instead of [1,1'-biphenyl]-4-ylmethanamine in step 3 of Example 1.

LC-MS m/z [M+H]⁺=244

Example 10. Synthesis of 5-((3-fluorobenzyl)amino)pyrimidine-4-carboxylic Acid

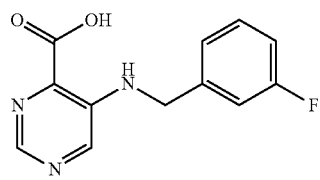 [SMILES: O=C(O)c1ncncc1NCc1cccc(F)c1]

The titled compound was synthesized with reference to the method illustrated in Example 1, except that an appropriate amine was used instead of [1,1'-biphenyl]-4-ylmethanamine in step 3 of Example 1.

LC-MS m/z [M+H]⁺=248

Example 11. Synthesis of 5-((2-fluorobenzyl)amino)pyrimidine-4-carboxylic Acid

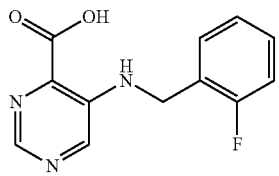 [SMILES: O=C(O)c1ncncc1NCc1ccccc1F]

The titled compound was synthesized with reference to the method illustrated in Example 1, except that an appropriate amine was used instead of [1,1'-biphenyl]-4-ylmethanamine in step 3 of Example 1.

LC-MS m/z [M+H]⁺=248

Example 12: Synthesis of 5-((1-propyl-1H-indazol-3-yl)amino)pyrimidine-4-carboxylic Acid

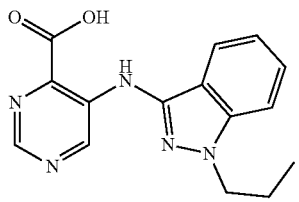 [SMILES: CCCn1nc(Nc2cncnc2C(=O)O)c2ccccc21]

Step 1: Ethyl 5-((1-propyl-1H-indazol-3-yl)amino)pyrimidine-4-carboxylate

Ethyl 5-bromopyrimidine-4-carboxylate (35.0 mg, 0.15 mmol), 1-propyl-1H-indazol-3-amine (31.5 mg, 0.18 mmol), K$_2$CO$_3$ (62 mg, 0.45 mmol) and toluene (1 mL) were charged in a sealed tube and the tube was then degassed. Xantphos (27 mg, 0.045 mmol) and Pd$_2$(dba)$_3$ (14 mg, 0.015 mmol) were added to the reaction solution, followed by stirring at 110° C. for 3 hours. After completion of the reaction, the reaction solution was allowed to cool to room temperature and filtered through a Celite pad using ethyl acetate. The filtrate was concentrated under reduced pressure and the obtained residue was purified by column chromatography (silica, MPLC:EtOAc:n-Hexane 20:80 to 50:50) to obtain the titled compound (29 mg, 59% yield) as a pale yellow solid.

LC-MS m/z [M+H]$^+$=326

Step 2: 5-((1-propyl-1H-indazol-3-yl)amino)pyrimidine-4-carboxylic Acid

Ethyl 5-((1-propyl-1H-indazol-3-yl)amino)pyrimidine-4-carboxylate (30 mg, 0.09 mmol) and LiCl (7.6 mg, 0.18 mmol) were added to a mix solution of methanol (1 mL), THF (1 mL) and H$_2$O (1 mL), followed by stirring at room temperature for 30 minutes. After completion of the reaction, the reaction solution was acidized with an aqueous 1N HCl solution. The acidified solution was extracted using a mix solution of chloroform/isopropanol (4:1). The collected organic layer was dried over anhydrous magnesium sulfate and filtered, and the solution was concentrated under reduced pressure to obtain the titled compound (25.4 mg, 96%) as a pale yellow solid.

$^1$H NMR (400 MHz, DMSO-d$_6$) δ 10.37 (s, 1H), 9.90 (s, 1H), 8.80 (s, 1H), 7.68-7.65 (m, 2H), 7.47 (td, J=8.0, 2.4 Hz, 1H), 7.18 (td, J=8.0, 2.4 Hz, 1H), 4.34 (t, J=8.0 Hz, 2H), 1.89 (sextet, J=8.0 Hz, 2H), 0.88 (t, J=8.0 Hz, 3H)

Example 13. Synthesis of 5-((1-(2-(dimethylamino)ethyl)-1H-indazol-3-yl)amino)pyrimidine-4-carboxylic Acid

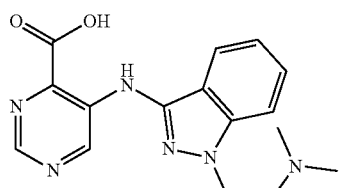

The titled compound was synthesized with reference to the method illustrated in Example 12.

LC-MS m/z [M+H]$^+$=327

Example 14. 5-((1-(3-benzamidopropyl)-1H-pyrazol-4-yl)amino)pyrimidine-4-carboxylic Acid

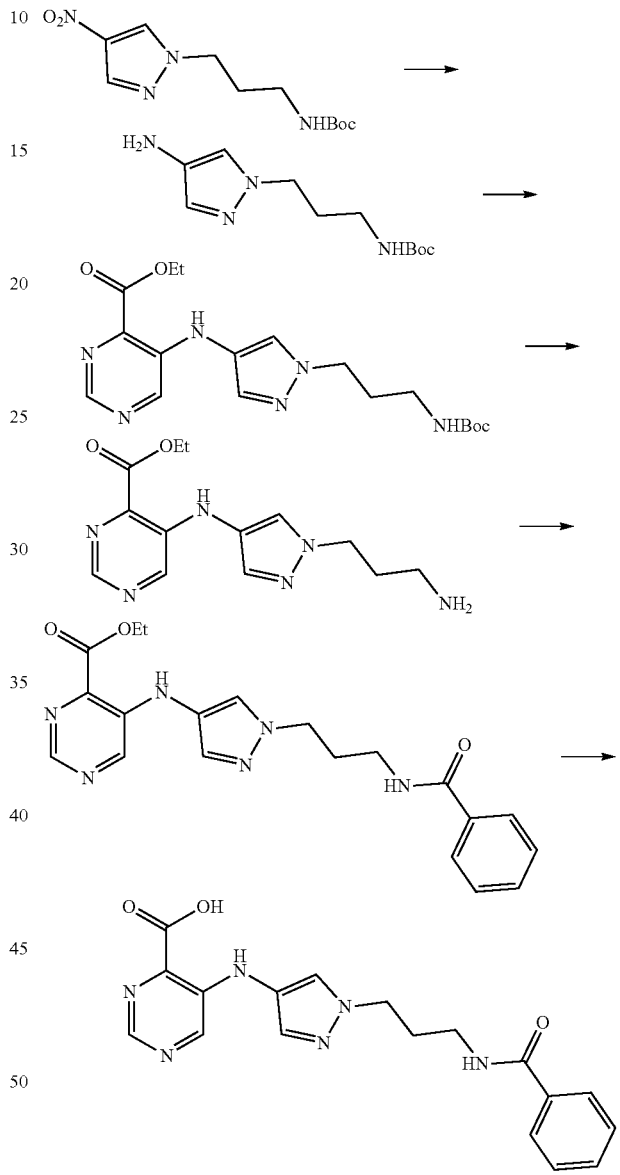

Step 1: Tert-butyl (3-(4-amino-1H-pyrazol-1-yl)propyl)carbamate 4-nitro-1H-pyrazole (678.0 mg, 6.0 mmol), 3-(Boc-amino)propyl bromide (1712.3 mg, 7.22 mmol), K$_2$CO$_3$ (1161.0 mg, 8.4 mmol) and acetonitrile (MeCN; 20 mL) were charged in a round-bottom flask, followed by stirring at 80° C. for 12 hours. After completion of the reaction, the reaction solution was allowed to cool to room temperature, was diluted with water and then extracted using ethyl acetate. The collected organic layer was dried over anhydrous magnesium sulfate and filtered, and the solution was concentrated under reduced pressure to obtain the titled compound (1,329.8 mg, 82% yield) as a pale yellow solid.
LC-MS m/z [M+H]$^+$=271

Step 2: Tert-butyl (3-(4-amino-1H-pyrazol-1-yl)propyl)carbamate

Tert-butyl (3-(4-nitro-1H-pyrazol-1-yl)propyl)carbamate (1,300.0 mg, 4.81 mmol) was dissolved in ethanol (16 mL) and then Pd/C (130.0 mg) was slowly added dropwise to the solution. The air was removed by injecting hydrogen gas into the reaction solution and the residue was stirred under a hydrogen gas atmosphere at room temperature for 18 hours. After completion of reaction, the reaction solution was washed with methanol and then filtered. The collected filtrate was concentrated under reduced pressure to obtain the titled compound (1,063.4 mg, 91% yield) as a pale yellow solid.
LC-MS m/z [M+H]$^+$=241

Step 3: Ethyl 5-((1-(3-tert-butoxycarbonyl)amino)propyl)-1H-pyrazol-4-yl)amino)pyrimidine-4-carboxylate Ethyl 5-bromopyrimidine-4-carboxylate (500 mg, 2.16 mmol), tert-butyl (3-(4-amino-1H-pyrazol-1-yl)propyl)carbamate (780 mg, 3.25 mmol), K$_2$CO$_3$ (894 mg, 6.48 mmol) and toluene (20 mL) were charged in a sealed tube and the tube was then degassed. Xantphos (375 mg, 0.648 mmol) and Pd$_2$(dba)$_3$ (434 mg, 0.22 mmol) were added to the reaction solution, followed by stirring at 110° C. for 3 hours. After completion of the reaction, the reaction solution was allowed to cool to room temperature filtered through a Celite pad using ethyl acetate. The filtrate was concentrated under reduced pressure and the obtained residue was purified by column chromatography (silica, MPLC:DCM:MeOH=100:0 to 90:10) to obtain the titled compound (550 mg, 66% yield) as a pale yellow solid.
LC-MS m/z [M+H]$^+$=391

Step 4: Ethyl 5-((1-(3-aminopropyl)-1H-pyrazol-4-yl)amino)pyrimidine-4-carboxylate 5-((1-(3-tert-butoxycarbonyl)amino)propyl)-1H-pyrazol-4-yl)amino)pyrimidine-4-carboxylate (356.8 mg, 0.91 mmol) was dissolved in dichloromethane (16.4 mL), and a hydrochloric acid solution (4.0M in 1,4-dioxane) was slowly added dropwise under stirring. When solids were sufficiently precipitated, the solvent was distilled under reduced pressure to obtain the titled compound (260.0 mg, 98% yield) as a pale yellow solid.
LC-MS m/z [M+H]$^+$=291.

Step 5: Ethyl 5-((1-(3-benzamidopropyl)-1H-pyrazol-4-yl)amino)pyrimidine-4-carboxylate 5-((1-(3-aminopropyl)-1H-pyrazol-4-yl)amino)pyrimidine-4-carboxylate (250.0 mg, 0.86 mmol) was dissolved in dichloromethane (20 mL), and benzoic acid (126 mg, 1.03 mmol), 1-[bis(dimethylamino)methylene]-1H-1,2,3-triazolo[4,5-b]pyridinium 3-oxide hexafluorophosphate (HATU; 490.2 mg, 1.29 mmol), hydroxybenzotriazole (HOBt; 197.4 mg, 1.29 mmol), and N,N-diisopropylethylamine (DIPEA; 332.8 mg, 2.58 mmol) were slowly added dropwise to the solution, followed by stirring at room temperature for 12 hours. After completion of the reaction, the reaction solution was diluted with water and the resulting solution was extracted using dichloromethane. The collected organic layer was dried over anhydrous magnesium sulfate and filtered, and the solution was concentrated under reduced pressure. The obtained residue was purified by column chromatography (silica, MPLC:DCM:MeOH 100:0 to 90:10) to obtain the titled compound (273 mg, 81% yield).
LC-MS m/z [M+H]$^+$=395

Step 6: 5-((1-(3-benzamidopropyl)-1H-pyrazol-4-yl)amino)pyrimidine-4-carboxylic Acid Ethyl 5-((1-(3-benzamidopropyl)-1H-pyrazol-4-yl)amino)pyrimidine-4-carboxylate (273 mg, 0.69 mmol) and LiOH (138 mg, 3.45 mmol) were added to a mix solution of methanol (3 mL), THF (3 mL) and H$_2$O (3 mL), followed by stirring at room temperature for 30 minutes. After completion of the reaction, the reaction solution was acidified with an aqueous 1N HCl solution. The acidified solution was extracted using a mix solution of chloroform/isopropanol (4:1). The collected organic layer was dried over anhydrous magnesium sulfate and filtered, and the solution was concentrated under reduced pressure to obtain the titled compound (127 mg, 50%)
$^1$H NMR (400 MHz, DMSO-d) δ 8.74 (s, 1H). 8.56 (d, J=5.6 Hz, 2H), 8.5 (t, J=5.2 Hz, 1H), 7.9 (s, 1H), 7.82 (d, J=7.2 Hz, 2H), 7.54 (s, 1H), 7.52-7.42 (m, 3H), 4.14 (t, J=6.8 Hz, 2H), 3.26 (q, J=6.8 Hz, 2H), 2.07-2.00 (m, 2H)

Example 15. Synthesis of 5-((1-methyl-1H-pyrazol-3-yl)amino)pyrimidine-4-carboxylic Acid

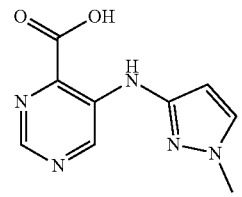 [SMILES: Cn1ccc(Nc2cncnc2C(=O)O)n1]

The titled compound was synthesized with reference to the method illustrated in Example 14.
LC-MS m/z [M+H]$^+$=220

Example 16. Synthesis of 5-((l-methyl-1H-pyrazol-4-yl)amino)pyrimidine-4-carboxylic Acid

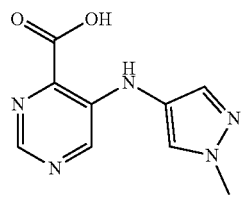 [SMILES: Cn1cc(Nc2cncnc2C(=O)O)cn1]

The titled compound was synthesized with reference to the method illustrated in Example 14.
LC-MS m/z [M+H]$^+$=220

Example 17. Synthesis of 5-(pyridazin-3-ylamino)pyrimidine-4-carboxylic Acid

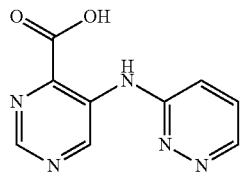 [SMILES: O=C(O)c1ncncc1Nc1cccnn1]

The titled compound was synthesized with reference to the method illustrated in Example 14.

LC-MS m/z [M+H]$^+$=218

Example 18. Synthesis of 5-(naphthalen-1-ylamino)pyrimidine-4-carboxylic Acid

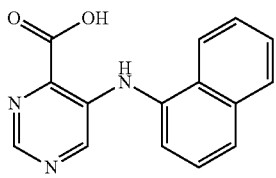 [SMILES: O=C(O)c1ncncc1Nc1cccc2ccccc12]

The titled compound was synthesized with reference to the method illustrated in Example 14.

LC-MS m/z [M+H]$^+$=266

Example 19. Synthesis of 5-((1-(3-(dimethylamino)propyl)-1H-pyrazol-4-yl)amino)pyrimidine-4-carboxylic Acid

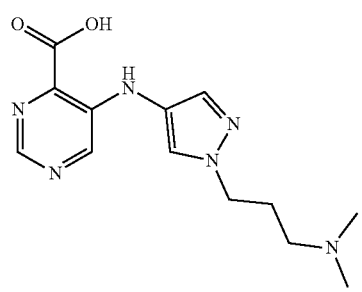 [SMILES: CN(C)CCCn1cc(Nc2cncnc2C(=O)O)cn1]

The titled compound was synthesized with reference to the method illustrated in Example 14.

LC-MS m/z [M+H]$^+$=291.

Example 20. Synthesis of 5-((4-(4-ethylpiperazin-1-yl)phenyl)amino)pyrimidine-4-carboxylic Acid

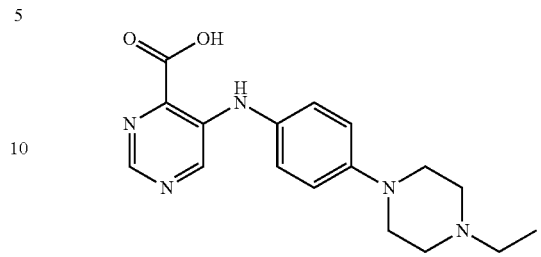

The titled compound was synthesized with reference to the method illustrated in Example 14.

LC-MS m/z [M+H]$^+$=328

Meanwhile, the novel compound represented by Formula 1 according to the present invention can be prepared into a variety of formulations depending on the purpose thereof.

Next, several formulation methods for incorporating the compound represented by Formula 1 according to the present invention as an active ingredient will be described in detail and the present invention is not limited thereto.

Preparation Example

Preparation 1: Tablet (Direct Pressing)

5.0 mg of an active ingredient was screened with a sieve, was mixed with 14.1 mg of lactose, 0.8 mg of Crospovidone USNF and 0.1 mg of magnesium stearate, and then pressed to prepare a tablet.

Preparation 2: Tablet (Wet Granulation)

5.0 mg of an active ingredient was screened with a sieve, and was mixed with 16.0 mg of lactose and 4.0 mg of starch. 0.3 mg of polysorbate 80 was dissolved in pure water and an appropriate amount of the resulting solution was added thereto, followed by granulation. After drying, the resulting granules were screened, and then mixed with 2.7 mg of colloidal silicon dioxide and 2.0 mg of magnesium stearate. The granules were pressed to prepare a tablet.

Preparation 3: Powder and Capsule 5.0 mg of an active ingredient was screened with a sieve, and then mixed with 14.8 mg of lactose, 10.0 mg of polyvinyl pyrrolidone, and 0.2 mg of magnesium stearate. The resulting mixture was charged into a hard No. 5 gelatin capsule using an appropriate apparatus.

Preparation 4: Injection 100 mg of an active ingredient was incorporated and 180 mg of mannitol, 26 mg of Na$_2$HPO$_4$-12H$_2$O and 2,974 mg of distilled water were incorporated to prepare an injection.

[Test Example] Evaluation of Biological Activity

Test Example 1. Measurement of Inhibitory Activity Against Histone Demethylase

Inhibitory activity against histone demethylase of the compound of the present invention was evaluated. In vitro $IC_{50}$ was calculated as inhibitory activity against KDM5A (lysine demethylase 5A) and shown in the following Table 1.

TABLE 1

| Subject compound | KDM5A (μM) |
|---|---|
| 5-((1-propyl-1H-indazol-3-yl)amino)pyrimidine-4-carboxylic acid (Example 12) | <3 |

Test Example 2. Measurement of Growth Inhibitory Activity on KDM5A-Overexpressed Cell Lines (MCF7)

The compound of the present invention was treated at a single concentration with KDM5A-overexpressed breast cancer cells, MCF7, and growth inhibitory activity was measured as an inhibition proportion (%). Results are shown in the following Table 2.

TABLE 2

| Subject compound | Growth inhibitory activity at 10 μM |
|---|---|
| 5-(([1,1'-biphenyl]-4-ylmethyl)amino)pyrimidine-4-carboxylic acid (Example 1) | B |

[Determination of inhibitory activity on cancer cell proliferation]
A: <40%,
B: 40~80%,
C: >80%

Test Example 3. Determination of Inhibitory Activity on Cancer Cell Proliferation The following test was conducted to identify whether the compound of the present invention has inhibitory activity on cancer cell proliferation.

The cancer cells herein used were lung cancer cell lines (NCI-H1299, A549) and breast cancer cell lines (MDA-MB-231).

Specifically, the NCI-H1299 cells were large cell lung carcinoma cell lines derived from human lung cancer tissues, and the MDA-MB231 cells were cell lines derived from human breast cancer tissues and obtained from the Korean cell line bank (KNCC, Seoul university), which were used for tests after passage culture. The NCI-H1299 and MDA-MB231 cell lines were cultured in a RPMI1640 medium supplemented with 10% FBS (fetal bovine serum), and were washed with buffered saline (PBS, pH 7.4), when the cells were proliferated on a plate at an affluence of 70 to 80%, and isolated into single cells using a 0.05% trypsin-EDTA (welgene) solution, and then passage-cultured at 1×10e6 cells/mL which were used for the test. 100 μL of NCI-H1299 and 100 μL of MDA-MB231 were seeded on a 96-well plate at 2×10e4 cells/mL, and 5×10e4 cells/mL, respectively, stabilized in the presence of $CO_2$ for 12 hours or longer, and then treated at different concentrations with the subject compound. After 72 hours, absorbance was measured using a CellTiter-Glo® Luminescent Cell Viability Assay (Promega) and an Envision 2103 multilabel reader (PerkinElmer). At this time, cells treated only with dimethylsulfoxide (DMSO) were used as the control group and relative viability (%) was calculated, based on 100% of the control group. $GI_{50}$ was obtained using Graph PRISM 6 software.

The inhibitory activity on cancer cell proliferation measured by the method is shown in the following Tables 3, 4 and 5.

TABLE 3

| Subject compound | NCI-H1299 inhibitory activity |
|---|---|
| 5-((3-fluorobenzyl)amino)pyrimidine-4-carboxylic acid (Example 10) | A |

[Determination of inhibitory activity on cancer cell proliferation]
A: $GI_{50}$ < 10 μM,
B: 10 μM < $GI_{50}$ < 100 μM,
C: $GI_{50}$ > 100 μM

TABLE 4

| Subject compound | A549 inhibitory activity |
|---|---|
| 5-((3,4-dichlorobenzyl)amino)pyrimidine-4-carboxylic acid (Example 3) | B |
| 5-((1-propyl-1H-indazol-3-yl)amino)pyrimidine-4-carboxylic acid (Example 12) | B |

[Determination of inhibitory activity on cancer cell proliferation]
A: $GI_{50}$ < 10 μM,
B: 10 μM < $GI_{50}$ < 100 μM,
C: $GI_{50}$ > 100 μM

TABLE 5

| Subject compound | MDA-MB-231 |
|---|---|
| 5-((3,4-dichlorobenzyl)amino)pyrimidine-4-carboxylic acid (Example 3) | B |
| 5-((4-fluorobenzyl)amino)pyrimidine-4-carboxylic acid (Example 6) | B |
| 5-((3,5-bis(trifluoromethyl)benzyl)amino)pyrimidine-4-carboxylic acid (Example 7) | B |
| 5-((4-methylbenzyl)amino)pyrimidine-4-carboxylic acid (Example 9) | B |
| 5-((1-propyl-1H-indazol-3-yl)amino)pyrimidine-4-carboxylic acid (Example 12) | B |

[Determination of inhibitory activity on cancer cell proliferation]
A: $GI_{50}$ < 10 μM,
B: 10 μM < $GI_{50}$ < 100 μM,
C: $GI_{50}$ > 100 μM

The invention claimed is:

1. A compound of Formula 1:

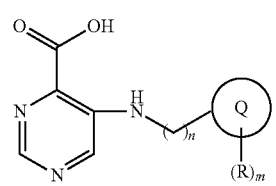

[Formula 1]

or a pharmaceutically acceptable salt thereof,
wherein:
Q is $C_6$-$C_{15}$ aryl or $C_4$-$C_{13}$ heteroaryl, wherein the heteroaryl contains 1, 2 or 3 heteroatom(s) selected from the group consisting of nitrogen, oxygen, and sulfur;

R is halogen, $C_1$-$C_{10}$ haloalkyl, $C_1$-$C_{10}$ alkoxy, 5- or 6-membered heterocycloalkyl, or —$(CH_2)_r$—$R^1$, wherein the $C_1$-$C_{10}$ haloalkyl is substituted with 1, 2, 3, 4, 5, 6, 7, 8, 9, 10, 11, 12 or 13 halogen(s) and the heterocycloalkyl contains 1 or 2 heteroatom(s) selected from the group consisting of nitrogen and oxygen;

$R^1$ is hydrogen, $C_1$-$C_{10}$ alkoxy, amino, mono($C_1$-$C_{10}$ alkyl)amino, di($C_1$-$C_{10}$ alkyl)amino, or —NHC(O)— phenyl;

m is 0, 1, 2 or 3;

n is 1, 2, 3, 4, 5 or 6; and r is 0, 1, 2, 3, 4, 5 or 6.

2. The compound according to claim 1, or a pharmaceutically acceptable salt thereof, wherein:

Q is phenyl, biphenyl, naphthalenyl, furanyl, thiophenyl, pyrazolyl, oxazolyl, isoxazolyl, pyridinyl, pyrimidinyl, pyridazinyl, or indazolyl;

R is chloro, fluoro, bromo, iodo, trifluoromethyl, methoxy, ethoxy, n-propoxy, isopropoxy, tert-butoxy, morpholinyl, piperidinyl, piperazinyl, or —$(CH_2)_r$—$R^1$; and $R^1$ is hydrogen, methoxy, ethoxy, propoxy, amino, methylamino, dimethylamino, diethylamino, or —NHC(O)-phenyl.

3. The compound according to claim 1, or a pharmaceutically acceptable salt thereof, wherein:

Q is phenyl, biphenyl, naphthalenyl, furanyl, thiophenyl, pyrazolyl, pyridazinyl, or indazolyl;

R is chloro, fluoro, trifluoromethyl, methoxy, methyl, ethyl, or propyl;

m is 0, 1 or 2; and n is 1.

4. A pharmaceutical composition comprising a pharmaceutically acceptable excipient and as an active ingredient a compound of Formula 1:

[Formula 1]

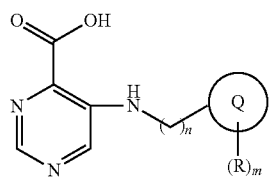

or a pharmaceutically acceptable salt thereof,
wherein:

Q is $C_6$-$C_{15}$ aryl or $C_4$-$C_{13}$ heteroaryl, wherein the heteroaryl contains 1, 2 or 3 heteroatom(s) selected from the group consisting of nitrogen, oxygen, and sulfur;

R is halogen, $C_1$-$C_{10}$ haloalkyl, $C_1$-$C_{10}$ alkoxy, 5- or 6-membered heterocycloalkyl, or —$(CH_2)_r$—$R^1$, wherein the $C_1$-$C_{10}$ haloalkyl is substituted with 1, 2, 3, 4, 5, 6, 7, 8, 9, 10, 11, 12 or 13 halogen(s) and the heterocycloalkyl contains 1 or 2 heteroatom(s) selected from the group consisting of nitrogen and oxygen;

$R^1$ is hydrogen, $C_1$-$C_{10}$ alkoxy, amino, mono($C_1$-$C_{10}$ alkyl)amino, di($C_1$-$C_{10}$ alkyl)amino, or —NHC(O)— phenyl;

m is 0, 1, 2 or 3;

n is 1, 2, 3, 4, 5 or 6; and r is 0, 1, 2, 3, 4, 5 or 6.

5. The pharmaceutical composition according to claim 4, wherein:

Q is phenyl, biphenyl, naphthalenyl, furanyl, thiophenyl, pyrazolyl, pyridazinyl, or indazolyl;

R is chloro, fluoro, bromo, iodo, trifluoromethyl, methoxy, ethoxy, n-propoxy, isopropoxy, tert-butoxy, morpholinyl, piperidinyl, piperazinyl, or —$(CH_2)_r$—$R^1$;

$R^1$ is hydrogen, methoxy, ethoxy, propoxy, amino, mono($C_1$-$C_{10}$ alkyl)amino, di($C_1$-$C_{10}$ alkyl)amino, or —NHC(O)-phenyl;

m is 0, 1 or 2; and n is 1.

6. The pharmaceutical composition according to claim 4, wherein:

Q is phenyl, biphenyl, naphthalenyl, furanyl, thiophenyl, pyrazolyl, pyridazinyl, or indazolyl;

R is chloro, fluoro, trifluoromethyl, methoxy, methyl, ethyl, or propyl;

m is 0, 1 or 2; and n is 1.

7. The pharmaceutical composition according to claim 4, wherein the compound of Formula 1 is selected from the group consisting of:

5-((furan-2-ylmethyl)amino)pyrimidine-4-carboxylic acid;

5-(((3-methylthiophen-2-yl)methyl)amino)pyrimidine-4-carboxylic acid;

5-((2-fluorobenzyl)amino)pyrimidine-4-carboxylic acid;

5-((3-fluorobenzyl)amino)pyrimidine-4-carboxylic acid;

5-((4-fluorobenzyl)amino)pyrimidine-4-carboxylic acid;

5-((4-methylbenzyl)amino)pyrimidine-4-carboxylic acid;

5-((4-methoxybenzyl)amino)pyrimidine-4-carboxylic acid;

5-((2,4-dimethoxybenzyl)amino)pyrimidine-4-carboxylic acid;

5-((3,4-dichlorobenzyl)amino)pyrimidine-4-carboxylic acid; and 5-((3,5-bis(trifluoromethyl)benzyl)amino)pyrimidine-4-carboxylic acid, or a pharmaceutically acceptable salt thereof.

8. A method for inhibiting cancer cell proliferation in a subject, comprising administering to a subject in need thereof a therapeutically effective amount of a compound of Formula 1:

[Formula 1]

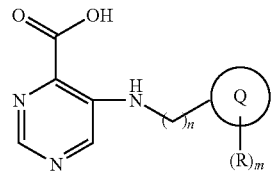

or a pharmaceutically acceptable salt thereof,
wherein:

Q is $C_6$-$C_{15}$ aryl or $C_4$-$C_{13}$ heteroaryl, wherein the heteroaryl contains 1, 2 or 3 heteroatom(s) selected from the group consisting of nitrogen, oxygen, and sulfur;

R is halogen, $C_1$-$C_{10}$ haloalkyl, $C_1$-$C_{10}$ alkoxy, 5- or 6-membered heterocycloalkyl, or —$(CH_2)_r$—$R^1$, wherein the $C_1$-$C_{10}$ haloalkyl is substituted with 1, 2, 3, 4, 5, 6, 7, 8, 9, 10, 11, 12 or 13 halogen(s) and the heterocycloalkyl contains 1 or 2 heteroatom(s) selected from the group consisting of nitrogen and oxygen;

$R^1$ is hydrogen, $C_1$-$C_{10}$ alkoxy, amino, mono($C_1$-$C_{10}$ alkyl)amino, di($C_1$-$C_{10}$ alkyl)amino, or —NHC(O)— phenyl;

m is 0, 1, 2 or 3;

n is 1, 2, 3, 4, 5 or 6; and r is 0, 1, 2, 3, 4, 5 or 6.

9. The method according to claim 8, wherein the subject has a cancer selected from the group consisting of melanoma, bladder cancer, breast cancer, lung cancer, and prostate cancer.

10. A compound selected from the group consisting of:

5-((4-(4-ethylpiperazin-1-yl)phenyl)amino)pyrimidine-4-carboxylic acid;

5-(naphthalen-1-ylamino)pyrimidine-4-carboxylic acid;

5-(pyridazin-3-ylamino)pyrimidine-4-carboxylic acid;

5-((1-methyl-1H-pyrazol-3-yl)amino)pyrimidine-4-carboxylic acid;

5-((1-methyl-1H-pyrazol-4-yl)amino)pyrimidine-4-carboxylic acid;

5-((1-(3-(dimethylamino)propyl)-1H-pyrazol-4-yl)amino)pyrimidine-4-carboxylic acid;

5-((1-(3-benzamidopropyl)-1H-pyrazol-4-yl)amino)pyrimidine-4-carboxylic acid;

5-((1-propyl-1H-indazol-3-yl)amino)pyrimidine-4-carboxylic acid;

5-((1-(2-(dimethylamino)ethyl)-1H-indazol-3-yl)amino)pyrimidine-4-carboxylic acid;

5-((furan-2-ylmethyl)amino)pyrimidine-4-carboxylic acid;

5-(((3-methylthiophen-2-yl)methyl)amino)pyrimidine-4-carboxylic acid;

5-((2-fluorobenzyl)amino)pyrimidine-4-carboxylic acid;

5-((3-fluorobenzyl)amino)pyrimidine-4-carboxylic acid;

5-((4-fluorobenzyl)amino)pyrimidine-4-carboxylic acid;

5-((4-methylbenzyl)amino)pyrimidine-4-carboxylic acid;

5-((4-methoxybenzyl)amino)pyrimidine-4-carboxylic acid;

5-(([1,1'biphenyl]-4-ylmethyl)amino)pyrimidine-4-carboxylic acid;

5-((2,4-dimethoxybenzyl)amino)pyrimidine-4-carboxylic acid;

5-((3,4-dichlorobenzyl)amino)pyrimidine-4-carboxylic acid; and 5-((3,5-bis(trifluoromethyl)benzyl)amino)pyrimidine-4-carboxylic acid, or a pharmaceutically acceptable salt thereof.

* * * * *